United States Patent [19]

Edwards et al.

[11] Patent Number: 5,554,110
[45] Date of Patent: Sep. 10, 1996

[54] MEDICAL ABLATION APPARATUS

[75] Inventors: Stuart D. Edwards, Los Altos; Ronald G. Lax, Grassvalley; Ingemar H. Lundquist, Pebble Beach; Hugh R. Sharkey, Redwood City; James A. Baker, Palo Alto, all of Calif.

[73] Assignee: Vidamed, Inc., Menlo Park, Calif.

[21] Appl. No.: 180,578

[22] Filed: Jan. 12, 1994

Related U.S. Application Data

[63] Continuation-in-part of Ser. No. 929,638, Aug. 12, 1992, abandoned, Ser. No. 12,370, Feb. 2, 1993, Pat. No. 5,370,675, Ser. No. 62,364, May 13, 1993, Pat. No. 5,435,805, and Ser. No. 61,647, May 13, 1993, Pat. No. 5,421,819.

[51] Int. Cl.$^6$ ..................................................... A61B 17/39
[52] U.S. Cl. ........................................................... 604/22
[58] Field of Search .............................. 604/164, 19–22, 604/53, 280; 601/2; 606/39, 45, 32; 607/96, 113, 115, 116, 138, 156, 101, 102

[56] References Cited

U.S. PATENT DOCUMENTS

| | | |
|---|---|---|
| Re. 32,066 | 1/1986 | Leveen . |
| 1,879,249 | 9/1932 | Hansaker ............................ 604/280 |
| 1,950,788 | 3/1934 | Ewerhardt et al. . |
| 1,968,997 | 8/1934 | Drucker . |
| 2,008,526 | 7/1935 | Wappler et al. . |

(List continued on next page.)

FOREIGN PATENT DOCUMENTS

| | | |
|---|---|---|
| 10858/92 | 8/1992 | Australia . |
| 219216A1 | 4/1987 | European Pat. Off. . |

(List continued on next page.)

OTHER PUBLICATIONS

Standard Urology Product Catalog, CIRCON ACMI: Stanford (1992).
Chang, Raymond J. et al, American Heart Journal, 125: 1276–1283 (May, 1993).
Cosman, Eric R. et al, Sterostatic and Functional Neurosurgery, pp. 2490–2499 (Date Unknown).
U.I. Dept. of Health and Human Services, MMWR 41: 401–404 vol. 41, No. 23, (Jun. 12, 1992).
Transuretheral μwave Thermotherapy for Prostatism: Early Mayo Foundation Experience: Blute, Mayo Clinic Proceedings: vol. 67 May 92 pp. 417–421.
New Therapies for Benign Prostatic Hyperplasia, Editorial Bruskewitz, Mayo Clinic Proceedings vol. 67 May 92 pp. 493–495.
Industry Strategies, Urology: "A Multi Billion Dollar Market . . . " Stephen Scala Nov. 19, 1991 pp. 1–32.
Diasonics, Brochure DIA 2000 171 CRF May 1988.
Perinchery, Narayan, "Neoplasms of the Prostate Gland." pp. 378–409 (Date Unknown).
Urology 5th ed., Storz, Jan. 1992.

*Primary Examiner*—Manuel Mendez
*Attorney, Agent, or Firm*—Flehr, Hohbach, Test, Albritton & Herbert

[57] ABSTRACT

A medical probe device including a catheter having a stylet guide housing with one or more stylet ports in a side wall thereof and a for directing a flexible stylet outward through the stylet port and through intervening tissue at a preselected, adjustable angle to a target tissue. The total catheter assembly includes a stylet guide lumen communicating with the stylet port and a stylet positioned in said stylet guide lumen for longitudinal movement from the port through intervening tissue to a target tissue. The stylet can be an electrical conductor enclosed within a non-conductive layer, the electrical conductor being a radio frequency electrode. During the ablation operation, the tissue immediately adjacent the stylet can become desiccated, thereby necessitating an increase of current flow and a loss of ablation efficiency. A forward and reverse movement of the non-conductive sleeve on the stylet during an operation frees the stylet from sticking tissue and creates a space around the electrode to allow the tissue to rehydrate.

14 Claims, 8 Drawing Sheets

U.S. PATENT DOCUMENTS

| | | |
|---|---|---|
| 2,022,065 | 11/1935 | Wappler . |
| 2,047,535 | 7/1936 | Wappler . |
| 2,118,631 | 5/1938 | Wappler . |
| 2,710,000 | 6/1955 | Cromer et al. . |
| 3,230,957 | 1/1966 | Seifert . |
| 3,339,542 | 9/1967 | Howell . |
| 3,556,079 | 1/1971 | Omizo et al. ............................ 128/2 |
| 3,595,239 | 7/1971 | Petersen . |
| 3,598,108 | 8/1971 | Jamshidi et al. . |
| 3,682,162 | 8/1972 | Colyer . |
| 3,828,780 | 8/1974 | Morrison, Jr. . |
| 3,835,842 | 9/1974 | Iglesias . |
| 3,840,016 | 10/1974 | Lindemann . |
| 3,850,175 | 11/1974 | Iglesias . |
| 3,858,577 | 1/1975 | Bass et al. . |
| 3,884,237 | 5/1975 | O'Malley et al. . |
| 3,924,628 | 12/1975 | Droegemueller et al. . |
| 3,939,840 | 2/1976 | Storz . |
| 3,941,121 | 3/1976 | Olinger et al. . |
| 3,942,530 | 3/1976 | Northeved . |
| 3,948,270 | 4/1976 | Hasson . |
| 3,991,770 | 11/1976 | Leveen . |
| 4,011,872 | 3/1977 | Komiya . |
| 4,119,102 | 10/1978 | Leveen . |
| 4,121,592 | 10/1978 | Whalley . |
| 4,136,566 | 1/1979 | Christensen . |
| 4,137,920 | 2/1979 | Bonnet . |
| 4,154,246 | 5/1979 | Leveen . |
| 4,204,549 | 5/1980 | Paglione . |
| 4,224,929 | 9/1980 | Furihata . |
| 4,228,809 | 10/1980 | Paglione .................................. 128/804 |
| 4,237,898 | 12/1980 | Whalley . |
| 4,267,828 | 5/1981 | Matsuo . |
| 4,295,467 | 10/1981 | Mann et al. . |
| 4,307,720 | 12/1981 | Weber, Jr. . |
| 4,311,143 | 1/1982 | Komiya ..................................... 606/47 |
| 4,311,145 | 1/1982 | Esty et al. . |
| 4,311,154 | 1/1982 | Sterzer et al. . |
| 4,312,364 | 1/1982 | Convert et al. . |
| 4,336,809 | 6/1982 | Clark . |
| 4,375,220 | 3/1983 | Matvias . |
| 4,397,314 | 8/1983 | Vaguine . |
| 4,402,311 | 9/1983 | Hattori . |
| 4,405,314 | 9/1983 | Cope . |
| 4,411,266 | 10/1983 | Cosman . |
| 4,448,198 | 5/1984 | Turner . |
| 4,452,236 | 6/1984 | Utsugi . |
| 4,470,407 | 9/1984 | Hussein ..................................... 606/2 |
| 4,494,539 | 1/1985 | Zenitani et al. . |
| 4,503,855 | 3/1985 | Maslanka .................................. 606/47 |
| 4,552,554 | 11/1985 | Gould et al. . |
| 4,562,838 | 1/1986 | Walker . |
| 4,565,200 | 1/1986 | Cosman . |
| 4,568,329 | 2/1986 | Mahurkar . |
| 4,580,551 | 4/1986 | Siegmund et al. . |
| 4,594,074 | 6/1986 | Anderson et al. . |
| 4,601,296 | 7/1986 | Yerushalmi . |
| 4,612,940 | 9/1986 | Kasevich et al. . |
| 4,658,836 | 4/1987 | Turner . |
| 4,660,560 | 4/1987 | Klein . |
| 4,669,475 | 6/1987 | Turner . |
| 4,672,962 | 6/1987 | Hershenson . |
| 4,676,258 | 6/1987 | Inokuchi et al. . |
| 4,681,122 | 7/1987 | Winters et al. . |
| 4,682,596 | 7/1987 | Bales et al. . |
| 4,697,595 | 10/1987 | Breyer et al. . |
| 4,700,716 | 10/1987 | Kasevich et al. . |
| 4,706,681 | 11/1987 | Breyer et al. . |
| 4,709,698 | 12/1987 | Johnston et al. . |
| 4,719,914 | 1/1988 | Johnson . |
| 4,753,223 | 6/1988 | Bremer . |
| 4,765,331 | 8/1988 | Petruzzi et al. . |
| 4,769,005 | 9/1988 | Ginsburg et al. . |
| 4,774,949 | 10/1988 | Fogarty . |
| 4,776,086 | 10/1988 | Kasevich et al. . |
| 4,781,186 | 11/1988 | Simpson et al. . |
| 4,784,638 | 11/1988 | Ghajar et al. . |
| 4,785,829 | 11/1988 | Convert et al. . |
| 4,798,215 | 1/1989 | Turner . |
| 4,800,899 | 1/1989 | Elliott . |
| 4,805,616 | 2/1989 | Pao . |
| 4,813,429 | 3/1989 | Eshel et al. . |
| 4,817,601 | 4/1989 | Roth et al. . |
| 4,818,954 | 4/1989 | Flachenecker et al. . |
| 4,822,333 | 4/1989 | Lavarenne . |
| 4,823,791 | 4/1989 | D'Amelio et al. . |
| 4,823,812 | 4/1989 | Eshel et al. . |
| 4,860,744 | 8/1989 | Johnson et al. . |
| 4,865,047 | 9/1989 | Chou et al. . |
| 4,872,458 | 10/1989 | Kanehira et al. . |
| 4,887,615 | 12/1989 | Taylor . |
| 4,893,623 | 1/1990 | Rosenbluth . |
| 4,896,671 | 1/1990 | Cunningham et al. . |
| 4,898,577 | 2/1990 | Badger . |
| 4,905,667 | 3/1990 | Foerster et al. . |
| 4,906,230 | 3/1990 | Maloney et al. . |
| 4,907,589 | 3/1990 | Cosman . |
| 4,911,148 | 5/1990 | Sosnowski et al. . |
| 4,911,173 | 3/1990 | Terwilliger . |
| 4,919,129 | 4/1990 | Weber, Jr. et al. . |
| 4,920,978 | 5/1990 | Colvin . |
| 4,932,958 | 6/1990 | Reddy et al. . |
| 4,936,281 | 6/1990 | Stasz . |
| 4,940,064 | 7/1990 | Desai . |
| 4,943,290 | 7/1990 | Rexroth ..................................... 606/49 |
| 4,946,449 | 8/1990 | Davis, Jr. . |
| 4,949,706 | 8/1990 | Thon . |
| 4,950,267 | 8/1990 | Ishihara et al. . |
| 4,955,377 | 9/1990 | Lennox et al. . |
| 4,961,435 | 10/1990 | Kitagawa et al. . |
| 4,966,597 | 10/1990 | Cosman . |
| 4,967,765 | 11/1990 | Turner et al. . |
| 4,982,724 | 1/1991 | Saito et al. . |
| 4,994,062 | 2/1991 | Nishigaki et al. . |
| 4,998,932 | 3/1991 | Rosen et al. . |
| 4,998,933 | 3/1991 | Eggers et al. . |
| 5,002,558 | 3/1991 | Klein et al. . |
| 5,003,991 | 4/1991 | Takayama et al. . |
| 5,007,437 | 4/1991 | Sterzer . |
| 5,007,908 | 4/1991 | Rydell . |
| 5,010,886 | 4/1991 | Passafaro et al. . |
| 5,026,959 | 6/1991 | Ito et al. . |
| 5,029,588 | 7/1991 | Yock et al. . |
| 5,030,227 | 7/1991 | Rosenbluth et al. . |
| 5,035,695 | 7/1991 | Weber, Jr. et al. . |
| 5,035,696 | 7/1991 | Rydell . |
| 5,045,056 | 9/1991 | Behl . |
| 5,045,072 | 9/1991 | Castillo . |
| 5,055,109 | 10/1991 | Gould et al. . |
| 5,057,105 | 10/1991 | Malone et al. . |
| 5,057,106 | 10/1991 | Kasevich et al. . |
| 5,057,107 | 10/1991 | Parins . |
| 5,059,851 | 10/1991 | Corl et al. . |
| 5,060,660 | 10/1991 | Gambale et al. . |
| 5,071,418 | 12/1991 | Rosenbaum ............................... 606/45 |
| 5,080,660 | 1/1992 | Buelna . |
| 5,083,565 | 1/1992 | Parins . |
| 5,084,044 | 1/1992 | Quint . |
| 5,100,423 | 3/1992 | Fearnot . |
| 5,108,415 | 4/1992 | Pinchuk et al. . |
| 5,109,859 | 5/1992 | Jenkins . |
| 5,116,615 | 5/1992 | Gokcen et al. . |

| | | |
|---|---|---|
| 5,120,316 | 6/1992 | Morales et al. . |
| 5,122,137 | 6/1992 | Lennox ......................... 606/42 |
| 5,135,525 | 8/1992 | Biscoping et al. . |
| 5,150,717 | 9/1992 | Rosen et al. . |
| 5,170,787 | 12/1992 | Lindegren . |
| 5,178,620 | 1/1993 | Eggers et al. . |
| 5,179,962 | 1/1993 | Dutcher et al. . |
| 5,190,539 | 3/1993 | Fletcher et al. . |
| 5,195,965 | 3/1993 | Shantha . |
| 5,195,968 | 3/1993 | Lundquist et al. . |
| 5,197,963 | 3/1993 | Parins ......................... 606/41 |
| 5,201,732 | 4/1993 | Parins et al. . |
| 5,207,672 | 5/1993 | Roth . |
| 5,220,927 | 6/1993 | Astrahan et al. . |
| 5,222,953 | 6/1993 | Dowlatshahi . |
| 5,228,441 | 7/1993 | Lundquist . |
| 5,234,004 | 8/1993 | Hascoet et al. ......... 607/102 |
| 5,235,964 | 8/1993 | Abenaim . |
| 5,249,585 | 10/1993 | Turner et al. ............ 607/99 |
| 5,254,088 | 10/1993 | Lundquist et al. . |
| 5,257,451 | 11/1993 | Edwards et al. . |
| 5,273,524 | 12/1993 | Fox et al. . |
| 5,273,535 | 12/1993 | Edwards et al. . |
| 5,275,162 | 1/1994 | Edwards et al. . |
| 5,281,213 | 1/1994 | Milder et al. . |
| 5,281,217 | 1/1994 | Edwards et al. . |
| 5,281,218 | 1/1994 | Imran . |
| 5,287,845 | 2/1994 | Faul et al. . |
| 5,290,286 | 3/1994 | Parins . |
| 5,293,868 | 3/1994 | Nardella . |
| 5,293,869 | 3/1994 | Edwards et al. . |
| 5,299,559 | 4/1994 | Bruce et al. . |
| 5,300,068 | 4/1994 | Rosar et al. . |
| 5,300,069 | 4/1994 | Hunsberger et al. . |
| 5,300,070 | 4/1994 | Gentelia et al. . |
| 5,300,099 | 4/1994 | Rudie . |
| 5,301,687 | 4/1994 | Wong et al. . |
| 5,304,134 | 4/1994 | Kraus et al. . |
| 5,304,214 | 4/1994 | Deford . |
| 5,309,910 | 5/1994 | Edwards et al. . |
| 5,312,392 | 5/1994 | Hofstetter et al. . |
| 5,313,943 | 5/1994 | Houser et al. . |

FOREIGN PATENT DOCUMENTS

| | | |
|---|---|---|
| 0370890 | 5/1990 | European Pat. Off. . |
| 0453071 | 10/1991 | European Pat. Off. . |
| 0495443 | 7/1992 | European Pat. Off. . |
| 521264A2 | 1/1993 | European Pat. Off. . |
| 2848484 | 5/1979 | Germany . |
| 2941060A1 | 4/1980 | Germany . |
| 3218314 | 6/1983 | Germany . |
| 3247793A1 | 7/1983 | Germany . |
| 3844131 | 12/1988 | Germany . |
| 3838840 | 5/1990 | Germany . |
| 2121675 | 5/1990 | Japan . |
| 9007303 | 7/1990 | WIPO . |
| WO911213 | 8/1991 | WIPO . |
| 9116859 | 11/1991 | WIPO ......................... 604/21 |
| 9207622 | 5/1992 | WIPO . |
| WO92/10142 | 6/1992 | WIPO . |
| 9221278 | 12/1992 | WIPO . |
| 9221285 | 12/1992 | WIPO . |
| 9304727 | 4/1993 | WIPO . |
| 9308756 | 5/1993 | WIPO . |
| 9308755 | 5/1993 | WIPO . |
| 9320893 | 10/1993 | WIPO . |
| 9308757 | 10/1993 | WIPO . |
| 9320767 | 10/1993 | WIPO . |
| 9320768 | 10/1993 | WIPO . |
| 9320886 | 10/1993 | WIPO . |
| WO93/25136 | 12/1993 | WIPO . |
| 9403759 | 2/1994 | WIPO . |
| 9404222 | 3/1994 | WIPO . |
| 9405226 | 3/1994 | WIPO . |
| 9406377 | 3/1994 | WIPO . |
| 9407410 | 4/1994 | WIPO . |
| 9407411 | 4/1994 | WIPO . |
| 9407412 | 4/1994 | WIPO . |
| 9407413 | 4/1994 | WIPO . |
| 9407441 | 4/1994 | WIPO . |
| 9407446 | 4/1994 | WIPO . |
| 9407549 | 4/1994 | WIPO . |

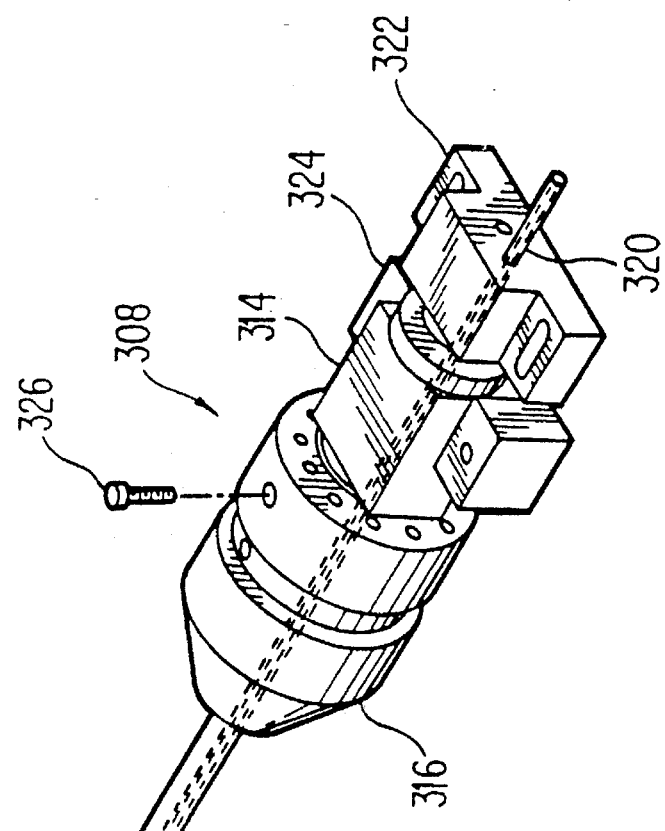
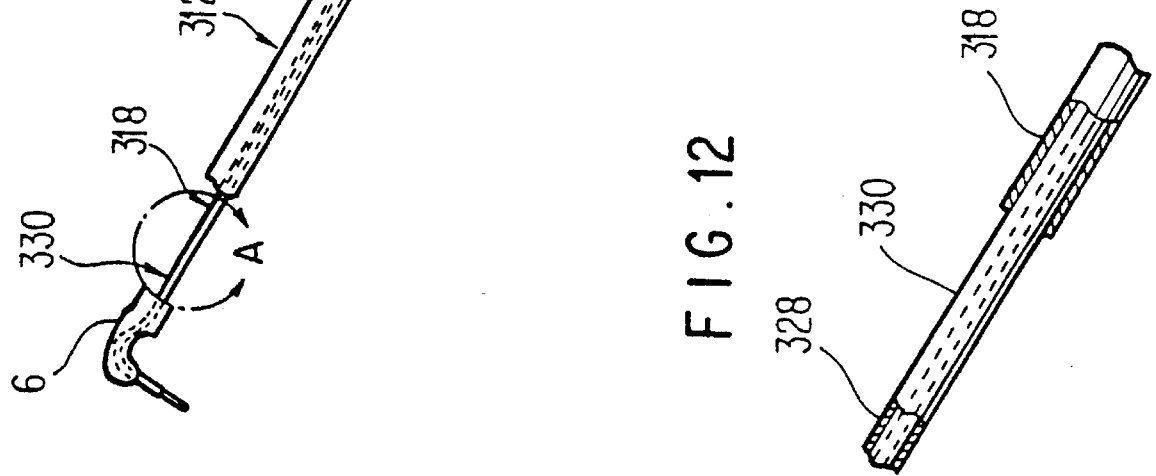

MEDICAL ABLATION APPARATUS

RELATIONSHIP TO COPENDING APPLICATION

This application is a continuation-in-part of applications Ser. No. 07/929,638 filed Aug. 12, 1992, now abandoned; Ser. No. 08/012,370 filed Feb. 2, 1993, now U.S. Pat. No. 5,370,675; Ser. No. 08/062,364 filed May 13, 1993, now U.S. Pat. No. 5,435,805; and Ser. No. 08/061,647 filed May 13, 1993, now U.S. Pat. No. 5,421,819. The entire contents of all of the above applications are hereby incorporated by reference.

FIELD OF THE INVENTION

This invention is directed to a unique device and method for penetrating body tissues for medical purposes such as tissue ablation and fluid substance delivery, for example. The device penetrates tissue to the precise target selected n order to deliver energy to the tissue and/or deliver substances. It limits this treatment to the precise preselected site, thereby minimizing trauma to normal surrounding tissue and achieving a greater medical benefit. This device is a catheter-like device for positioning a treatment assembly in the area or organ selected for medical treatment with one or more stylers in the catheter, mounted for extension from a stylet port in the side of the catheter through surrounding tissue to the tissue targeted for medical intervention.

Specifically, this invention related to a method and apparatus for separating or unsticking an operating stylet emitting electromagnetic energy from the body tissue being ablated to allow for rehydration of the immediately contiguous tissue.

BACKGROUND OF THE INVENTION

Treatment of cellular tissues usually requires direct contact of target tissue with a medical instrument, usually by surgical procedures exposing both the target and intervening tissue to substantial trauma. Often, precise placement of a treatment probe is difficult because of the location of targeted tissues in the body or the proximity of the target tissue to easily damaged, critical body organs, nerves, or other components.

Benign prostatic hypertrophy or hyperplasia (BPH), for example, is one of the most common medical problems experienced by men over 50 years old. Urinary tract obstruction due to prostatic hyperplasia has been recognized since the earliest days of medicine. Hyperplastic enlargement of the prostate gland often leads to compression of the urethra, resulting in obstruction of the urinary tract and the subsequent development of symptoms including frequent urination, decrease in urinary flow, nocturia, pain, discomfort, and dribbling. The association of BPH with aging has been shown to exceed 50% in men over 50 years of age and increases in incidence to over 75% in men over 80 years of age. Symptoms of urinary obstruction occur most frequently between the ages of 65 and 70 when approximately 65% of men in this age group have prostatic enlargement.

Currently there is no proven effective nonsurgical method of treatment of BPH. In addition, the surgical procedures available are not totally satisfactory. Currently patients suffering from the obstructive symptoms of this disease are provided with few options: continue to cope with the symptoms (i.e., conservative management), submit to drug therapy at early stages, or submit to surgical intervention.

More than 430,000 patients per year undergo surgery for removal of prostatic tissue in the United States. These represent less than five percent of men exhibiting clinical significant symptoms.

Those suffering from BPH are often elderly men, many with additional health problems which increase the risk of surgical procedures. Surgical procedures for the removal of prostatic tissue are associated with a number of hazards including anesthesia related morbidity, hemorrhage, coagulopathies, pulmonary emboli and electrolyte imbalances. These procedures performed currently can also lead to cardiac complications, bladder perforation, incontinence, infection, urethral or bladder neck stricture, retention of prostatic chips, retrograde ejaculation, and infertility. Due to the extensive invasive nature of the current treatment options for obstructive uropathy, the majority of patients delay definitive treatment of their condition. This circumstance can lead to serious damage to structures secondary to the obstructive lesion in the prostate (bladder hypertrophy, hydronephrosis, dilation of the kidney pelves, chronic infection, dilation of ureters, etc.) which is not without significant consequences. In addition, a significant number of patients with symptoms sufficiently severe to warrant surgical intervention are therefore poor operative risks and are poor candidates for prostatectomy. In addition, younger men suffering from BPH who do not desire to risk complications such as infertility are often forced to avoid surgical intervention. Thus the need, importance and value of improved surgical and non-surgical methods for treating BPH is unquestionable.

High-frequency currents are used in electrocautery procedures for cutting human tissue especially when a bloodless incision is desired or when the operating site is not accessible with a normal scalpel but presents an access for a thin instrument through natural body openings such as the esophagus, intestines or urethra. Examples include the removal of prostatic adenomas, bladder tumors or intestinal polyps. In such cases, the high-frequency current is fed by a surgical probe into the tissue to be cut. The resulting dissipated heat causes boiling and vaporization of the cell fluid at this point, whereupon the cell walls rupture and the tissue is separated.

Destruction of cellular tissues in situ has been used in the treatment of many diseases and medical conditions alone or as an adjunct to surgical removal procedures. It is often less traumatic than surgical procedures and may be the only alternative where other procedures are unsafe. Ablative treatment devices have the advantage of using an electromagnetic energy which is rapidly dissipated and reduced to a non-destructive level by conduction and convection forces of circulating fluids and other natural body processes.

Microwave, radio frequency, acoustical (ultrasound) and light energy (laser) devices, and tissue destructive substances have been used to destroy malignant, benign and other types of cells and tissues from a wide variety of anatomic sites and organs. Tissues treated include isolated carcinoma masses and, more specifically, organs such as the prostate, glandular and stromal nodules characteristic of benign prostate hyperplasia. These devices typically include a catheter or cannula which is used to carry a radio frequency electrode or microwave antenna through a duct to the zone of treatment and apply energy diffusely through the duct wall into the surrounding tissue in all directions. Severe trauma is often sustained by the duct wall during this cellular destruction process, and some devices combine cooling systems with microwave antennas to reduce trauma to the ductal wall. For treating the prostate with these devices, for example, heat energy is delivered through the walls of the urethra into the surrounding prostate cells in an effort to ablate the tissue causing the constriction of the urethra. Light energy, typically from a laser, is delivered to prostate tissue target sites by "burning through" the wall of the urethra. Healthy cells of the duct wall and healthy tissue between the nodules and duct wall are also indiscriminately destroyed in the process and can cause unnecessary loss of some prostate function. Furthermore, the added cooling function of some microwave devices complicates the apparatus and requires that the device be sufficiently large to accommodate this cooling system.

Application of liquids to specific tissues for medical purposes is limited by the ability to obtain delivery without traumatizing intervening tissue and to effect a delivery limited to the specific target tissue. Localized chemotherapy, drug infusions, collagen injections, or injections of agents which are then activated by light, heat or chemicals would be greatly facilitated by a device which could conveniently and precisely place a fluid (liquid or gas) supply catheter opening at the specific target tissue.

A patent to Weber U.S. Pat. No. 4,307,720, issued Dec. 29, 1981, discloses the scraping of an electrode blade by sliding the electrode back into the body housing. However, this patent requires that the scraping edge be rigid to effect the desired scraping, and, further, the patent is not related to rehydration of ablation tissue nor to the creation of space between the ablation tissue and the operating stylet.

The previously filed patent applications cited above, hereby incorporated by reference, disclose a medical probe device which comprises a catheter having a stylet guide housing with at least one stylet port in a side thereof and stylet guide apparatus for directing a flexible stylet outward through at least one stylet port and through intervening tissue to targeted tissues. The stylet guide housing has an optical viewer positioned for viewing the stylet which includes a fiber optic channel for receiving a fiber optic viewing device. The device preferably includes a flushing liquid channel in the stylet guide housing having an exit port positioned to direct flushing liquid issuing therefrom across the end of the fiber optic device when positioned in the viewing zone. The stylet comprises an electrical conductor enclosed within a non-conductive sleeve, the electrical conductor being a radio frequency electrode.

Upon application of the RF power and the ablation operation proceeds, sometimes the tissue being ablated sticks to the stylet electrode as the tissue contiguous therewith becomes desiccated due to the RF current flowing in the tissue. This increases the impedance to the current flowing from the stylet which necessitates an increase of applied power and lowers the efficiency of the ablation operation.

OBJECTS AND SUMMARY OF THE INVENTION

It is an object of this invention to provide a device and method for penetrating tissue, through intervening tissues to the precise target tissue selected for a medical action such as tissue ablation and/or substance delivery, limiting this activity to the precise preselected site, thereby minimizing the trauma and achieving a greater medical benefit.

It is another object of this invention is to unstick or disengage and rehydrate the tissue being ablated by a device and method for tissue ablation of body tissues which delivers the therapeutic energy directly into targeted tissues while minimizing effects on its surrounding tissue.

It is a further object of this invention to reopen the space immediately adjacent the stylet electrode and extend the time that the device for tissue ablation can be operated in the targeted tissue.

In summary, the method of medical treatment of this invention includes the following steps. Introducing a catheter to a zone adjacent to said tissue mass to be treated. Moving a flexible stylet from the catheter through a catheter port in the sidewall of the catheter and through surrounding tissue into said target tissue to be treated, said stylet being a conductive electrode at least partially enclosed within a non-conductive sleeve in a first position for preventing significant transfer of current from the electrode to tissue surrounding the sleeve. Moving the non-conductive sleeve from said first position to a second position to expose said electrode in the target tissue to be treated, generating heat in the target tissue by passing electrode current from the preselected area of the electrode into the target tissue. Selectively moving said non-conductive sleeve from said second position to said first position and reverse to clear away any treated tissue from said electrode. Monitoring the desiccation of the tissue immediately adjacent the stylet during the medical treatment, and initiating a forward and reverse movement of the non-conductive sleeve on the stylet to free the stylet from sticking tissue and create a space around the electrode to allow the tissue to rehydrate.

Another embodiment for ablative treatment of a target tissue includes these steps. Advancing an electrical conductor through surrounding tissue into said target tissue to be ablated, the conductor being a flexible stylet surrounded by a movable non-conductive sleeve for preventing a significant transfer of energy from the conductor to tissue surrounding the sleeve. Moving the non-conductive sleeve to remove it from a first position on said conductor to a second position on said conductor positioned in the target tissue to be treated. Generating heat in the target tissue from an electric current from said conductor. Selectively moving said non-conductive sleeve from said second position to said first position and return to clear away any treated tissue from said conductor. Further steps include monitoring the current flow in said target tissue during the step of generating heat to detect a condition wherein said target tissue is drying excessively and then initiating said step of selectively moving said non-conductive sleeve; and rehydrating said target tissue by natural or artificial means.

BRIEF DESCRIPTION OF THE DRAWINGS

FIG. 11 is an isometric view of the adjuster block and tension tube assembly of the RF ablation catheter shown in FIG. 10.

FIG. 12 is a detailed view "A" of the tension tube connections shown in FIG. 11.

DETAILED DESCRIPTION OF THE INVENTION

Figure 1:
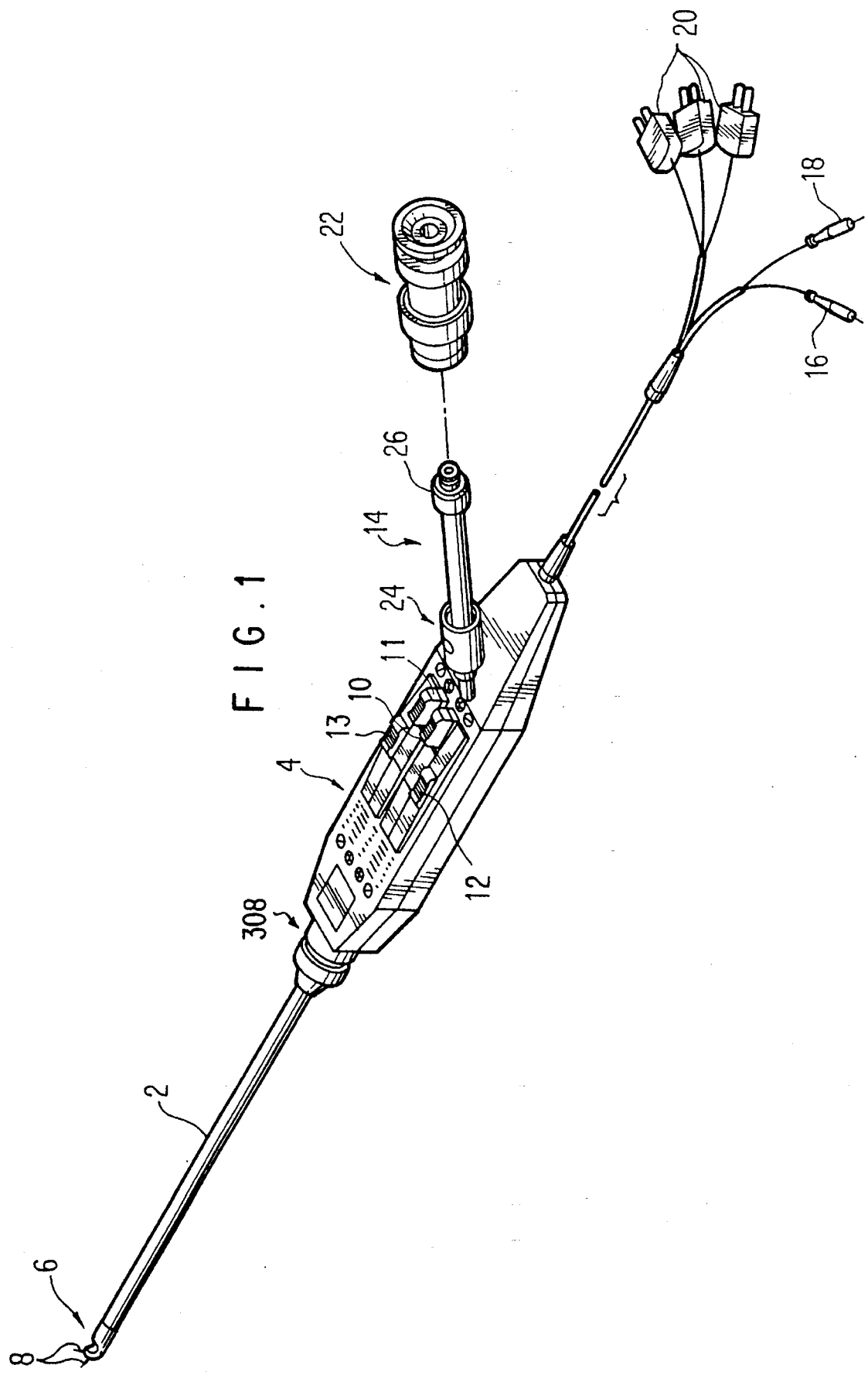
FIG. 1 is an isometric view of an RF ablation catheter embodiment of this invention with an fiber optic viewing accessory.

The device of this invention provides a precise controlled positioning of a treatment stylet in a tissue targeted for treatment, destruction or sampling from a catheter positioned in the vicinity of the target tissue.

The term "stylet" as used herein is defined to include both solid and hollow probes which are desired to be passed from a catheter port through normal tissue to targeted tissues. The stylet is shaped to facilitate easy passage through tissue. It can be a solid wire, thin rod, or other solid shape or it can be a thin hollow tube or other shape having a longitudinal lumen for introducing fluids to or removing materials from a site. The stylet can also be a thin hollow tube or other hollow shape, the hollow lumen thereof containing a reinforcing or functional rod or tube such as a laser fiber optic. The stylet preferably has a sharpened end to reduce resistance and trauma when it is pushed through tissue to a target site.

The stylet can be designed to provide a variety of medically desired treatments of a selected tissue. As a radio frequency electrode or microwave antenna, it can be used to ablate or destroy targeted tissues. As a hollow tube, it can be used to deliver a treatment fluid such as a liquid to targeted tissues. The liquid can be a simple solution or a suspension of solids, for example, colloidal particles, in a liquid. Since the stylet is very thin, it can be directed from the catheter through intervening normal tissue with a minimum of trauma to the normal tissue.

The device and method of this invention provide a more precise, controlled medical treatment which is suitable for destroying cells of medically targeted tissues throughout the body, both within and external to body organs. The device and method are particularly useful for treating benign prostate hyperplasia (BPH), and the device and its use are hereinafter described with respect to BPH, for purposes of simplifying the description thereof. It will be readily apparent to a person skilled in the art that the device and method can be used to destroy body tissues in any body cavities or tissue locations that are accessible by percutaneous or endoscopic catheters, and is not limited to the prostate. Application of the device and method in all of these organs and tissues are intended to be included within the scope of this invention.

BPH is a condition which arises from the replication and growth of cells in the prostate and the decrease of cell death rate, forming glandular and stromal nodules which expand the prostate and constrict the opening of the prostatic urethra. Glandular nodules are primarily concentrated within the transition zone, and stromal nodules within the periurethral region. Traditional treatments of this condition have included surgical removal of the entire prostate gland, digital removal of the adenoma, as well as transurethral resection of the urethral canal and prostate to remove tissue and widen the passageway. One significant and serious complication associated with these procedures is iatrogenic sterility. More recently, laser treatment has been employed to remove tissue, limiting bleeding and loss of body fluids. Balloons have also been expanded within the urethra to enlarge its diameter, with and without heat, but have been found to have significant limitations.

Microwave therapy has been utilized with some success by positioning a microwave antenna within the prostatic urethra and generating heat in the tissue surrounding the urethra with an electromagnetic field. Coolants are sometimes applied within the catheter shaft to reduce the temperature of the urethral wall. This necessitates complicated mechanisms to provide both cooling of the immediately adjacent tissues while generating heat in the more distant prostatic tissue. This technique is similar to microwave hyperthermia. Similarly, radio frequency tissue ablation with electrodes positioned within the urethra exposes the urethral wall to destructive temperatures. To avoid this, low temperature settings required to protect the urethra must be so low that the treatment time required to produce any useful effect is unduly extended, e.g. up to three hours of energy application.

One embodiment of the device of this invention uses the urethra to access the prostate and positions RF electrode stylets directly into the tissues to be destroyed. The portion of the stylet conductor extending from the urethra to targeted tissues is enclosed within a longitudinally adjustable sleeve shield which prevents exposure of the tissue adjacent to the sleeve to the RF current. The sleeve movement is also used to control the amount of energy per unit surface area which is delivered by controlling the amount of electrode exposed. Thus the ablative destruction is confined to the tissues targeted for destruction, namely those causing the constriction. Other aspects of the invention will become apparent from the drawings and accompanying descriptions of the device and method of this invention. It will be readily apparent to a person skilled in the art that this procedure can be used in many areas of the body for percutaneous approaches and approaches through body orifices.

FIG. 1 is an isometric view of an RF ablation catheter embodiment of this invention with a fiber optic viewing accessory. The flexible catheter 2, attached to handle 4, has a terminal stylet guide 6 with two stylets 8. The handle has stylet electrode tabs 10 and 11 and sleeve tabs 12 and 13 as will be described in greater detail hereinafter. The handle 4 is also connected to a optical viewing assembly 14 and RF power connector 16, transponder connector 18 and thermocouple connectors 20. The portions of the catheter 2 leading from the handle 4 to the stylet guide tip 6 can optionally have a graduated stiffness. For example, the catheter can be designed to be more stiff near the handle and more flexible near the tip, or any other stiffness profiles. The catheter can be constructed of an inner slotted stainless steel tube with outer flexible sleeve such as is described in U.S. Pat. No. 5,322,064 the entire contents of which are incorporated herein by reference. It can also be made of coiled or braided wire to which an outer sleeve is bonded.

The fiber optic viewing assembly in this embodiment includes a lens focusing assembly 22, a lens viewing assembly support connector 24 assembly attached to a male quick disconnect connector 26 by flexible tubing 28.

Figure 2:
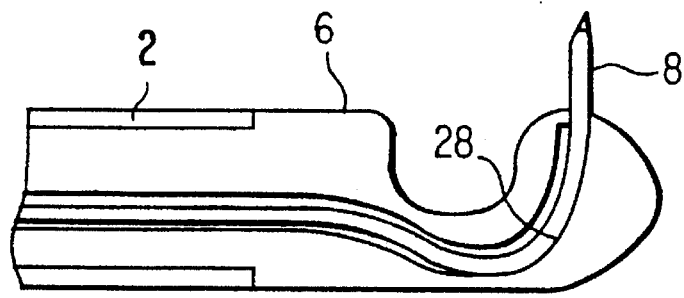
FIG. 2 is a cross-sectional view of a catheter of FIG. 1 showing details of the stylet guide housing.

FIG. 2 is a cross-sectional view of a catheter of FIG. 1 showing details of the stylet guide housing. The stylet guide housing 6 has a curved passageway 28 through which the stylet 8 is extended into the tissue to be treated. Further details of these components are described in copending applications Ser. No. 08/012,370 filed Feb. 2, 1993, and application Ser. No. 08/062,647 filed May 13, 1993.

Figure 3:
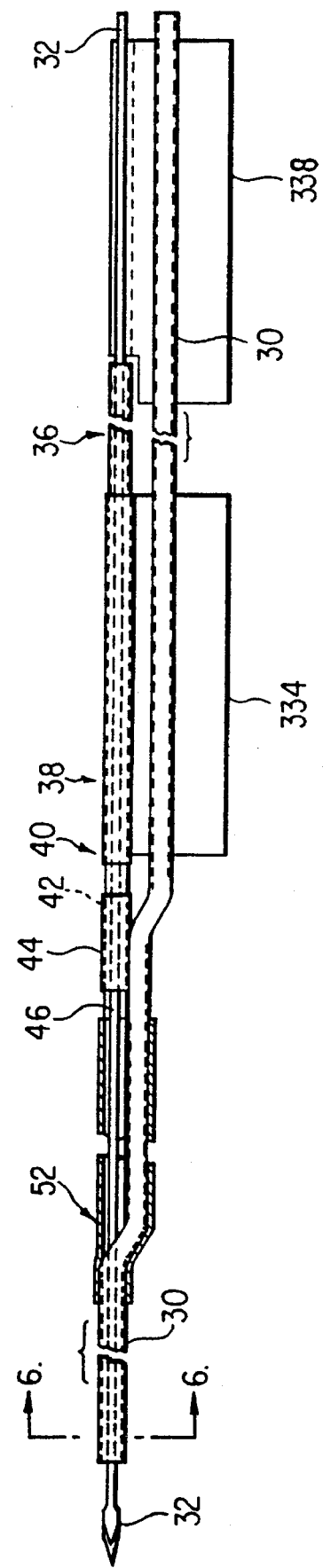
FIG. 3 is a side view of the stylet and lumen assembly of this invention.

FIG. 3 is a side view of the stylet and lumen assembly of this invention. The key components of the stylet of this embodiment are an insulating sleeve 30 and an electrode 32 extending therethrough. The electrode 32 has a sharpened tip, in this embodiment a broadened spear tip. The proximal end of the electrode and sleeve are connected by respective sleeve connector 334 and electrode connector 338 to handle sleeve and electrode slides described in greater detail hereinafter with respect to FIGS. 10 and 13. An electrode support tube 36 extends from the electrode connector 338 to the area 38 of the sleeve connector 334 to transmit compressive pressure without collapsing the electrode 32. An insulating sleeve support tube 40 made of shrink tubing extends from the sleeve connector 334 to the beginning or proximal end 42 of the outer tubing 44. Tubing 44 joins the support tubing to the control tube 46. The control tube 46 supporting both the electrode and insulating sleeve extends to the junction 48 (see FIG. 4) of the electrode lumen passageway 50 and the electrode 32. In this manner, support is provided over the length of the stylet extending from the handle to the trilumen tip, preventing collapse or loss of linearity of the highly flexible electrode when it is pushed through the stylet guide housing.

Figure 5:
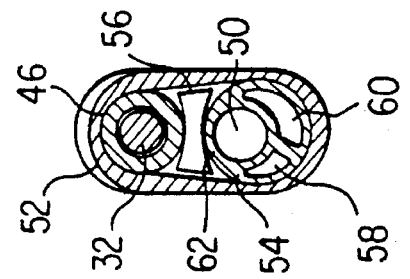
FIG. 5 is a cross-sectional view of the junction of the stylet and control tube assembly taken along the line 5—5 of FIG. 4.
Figure 4:
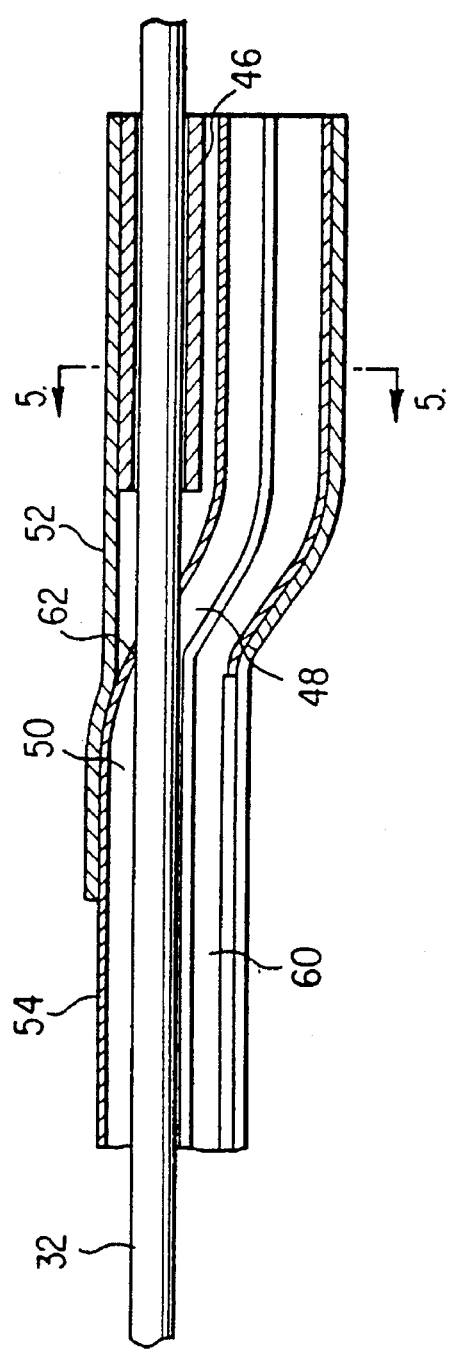
FIG. 4 is a cross-sectional side view of the of the junction of the stylet and control tube assembly taken along the central axis of the tubing.

FIG. 4 is a side elevational view in section of the junction of the stylet and control tube assembly along the central axis of the tubing, and FIG. 5 is a cross-sectional view of the junction of the stylet and control tube assembly taken along the line 5—5 of FIG. 4. At the junction 48, the electrode 32 extends through the upper electrode lumen wall 62 and enters the electrode lumen 50. The outer tubing 52 encloses and supports both the distal ends of the control tubing 46 a and trilumen sleeve tube 54.

Referring to FIG. 5, the space 56 between the control tube 46 and the trilumen sleeve tube 54 can be filled with and adhesive to secure them together. The sleeve tube 54 includes an electrode lumen 50, a temperature sensor lumen 58 and a fluid supply lumen 60 for supply of optional fluids such as antibiotics or anesthetics to the area of treatment.

Figure 6:
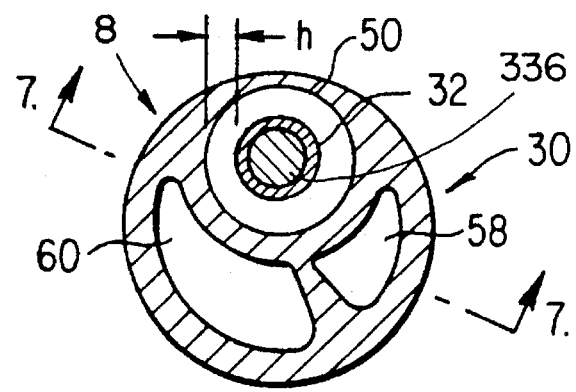
FIG. 6 is a cross-sectional view of a trilumen stylet of this invention taken along the line 6—6 in FIG. 3.

FIG. 6 is a cross-sectional view of a trilumen stylet of this invention taken along the line 6—6 in FIG. 3. The trilumen sleeve 30 is an insulating sleeve for the electrode 32 and includes the additional temperature sensor lumen 58 and liquid supply lumen 60. The inner surface of the electrode lumen 50 can be spaced from the outer surface of the electrode by a distance "h" which can be, for example, from about 1 to 3 mm to define an additional liquid supply conduit with an approximate annular cross-section.

Figure 7:
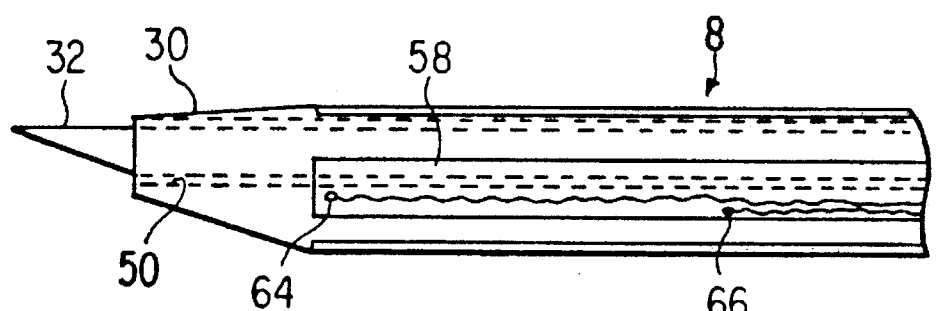
FIG. 7 is a cross-sectional side view of the trilumen stylet tip shown in FIG. 3 taken along line 7—7 of FIG. 6.

FIG. 7 is a cross-sectional side view of the trilumen stylet tip shown in FIG. 6 taken along the line 7—7. The terminal end of the temperature sensor lumen 58 is sealed to protect the electrical components. Thermocouple 64 is placed at the distal end of the sleeve 30 to monitor the temperature of the tissue surrounding the electrode 32 and is preferably less than about 1 mm from the exposed electrode. Thermocouple 66 is placed at least 3 mm and preferably from about 3 to 6 mm from the tip of sleeve 30 to monitor the temperature of the duct wall (such as the urethra) through which the stylet is extended. This is provided to ensure the duct wall temperature does not reach destructive levels when the RF treatment of tissue surrounding the extended electrode is underway.

Figure 8:
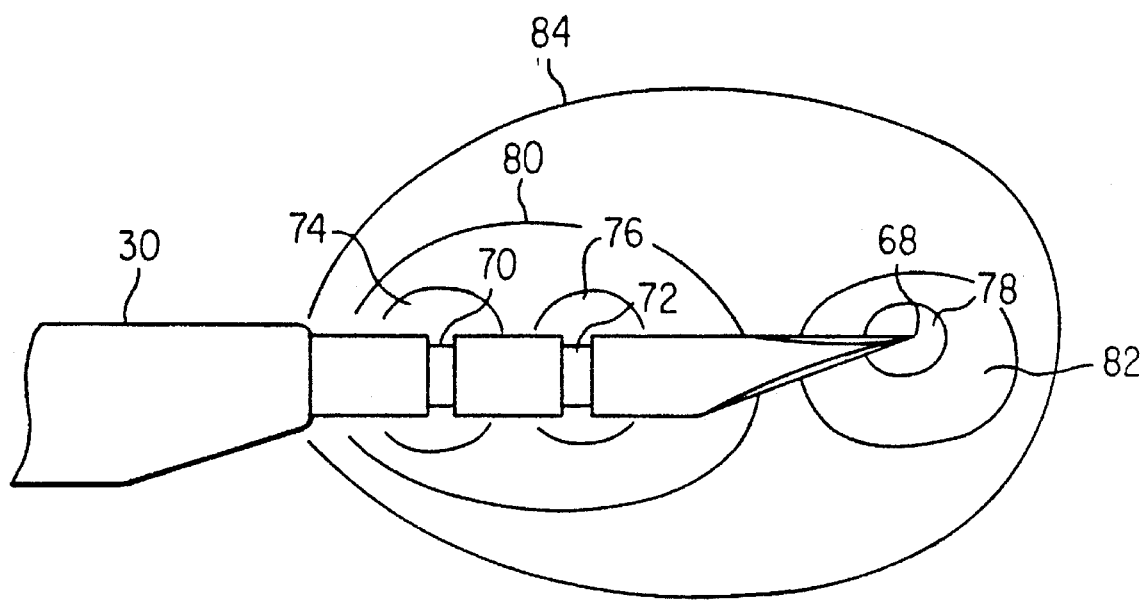
FIG. 8 is a plane view of the annular groove embodiment of the current density focusing electrode of this invention.

FIG. 8 is a plane view of the annular groove embodiment of the current density focusing electrode of this invention. In this embodiment, the electrode is ground to a single current focusing sharp tip 68 without secondary corner or other sharp edges which could also focus or crowd current. Additional current focusing can be provided along the electrode surface by the annular grooves 70 and 72. The temperature of the tissue surrounding the electrode initially increase in initial zones 74, 76 and 78. The elevated temperature zone then extends to two intermediate zones 80 and 82, as the zones from the grooves merge. Thereafter all of the elevated temperature zones merge to form the single oval zone lesion 84. Use of these current focusing grooves 70 and 72 produces a more symmetrical lesion.

Figure 9:
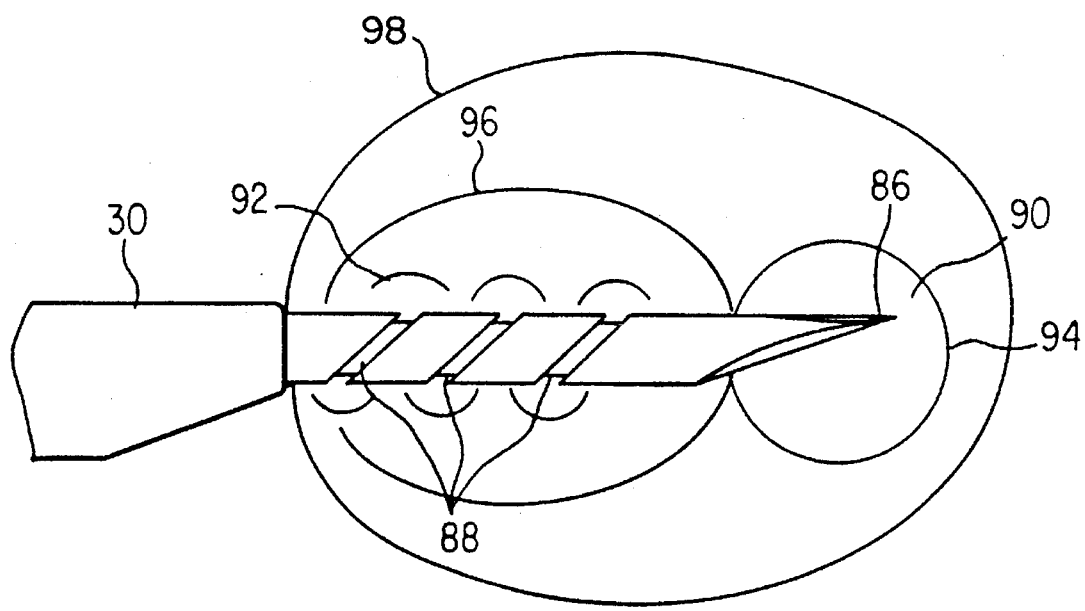
FIG. 9 is a plane view of the spiral groove embodiment of the current density focusing electrode of this invention.

FIG. 9 is a plane view of the spiral groove embodiment of the current density focusing electrode of this invention. In this embodiment, the electrode is also ground to a single current focusing sharp tip 86 without secondary sharp corners or edges which could also focus or crowd current. Additional current focusing can be provided along the electrode surface by at least one spiral or helical groove 88. The temperature of the tissue surrounding the electrode initially increases in the initial tip zone 90 and spiral zone 92. The elevated temperature zone then extends to two intermediate zones 94 and 96, as the spiral zone 92 merges to form a single zone 96. Thereafter, all of the elevated temperature zones merge to form the single oval zone lesion 98. Use of the spiral focusing groove 88 provides a more symmetrical lesion.

Figure 10:
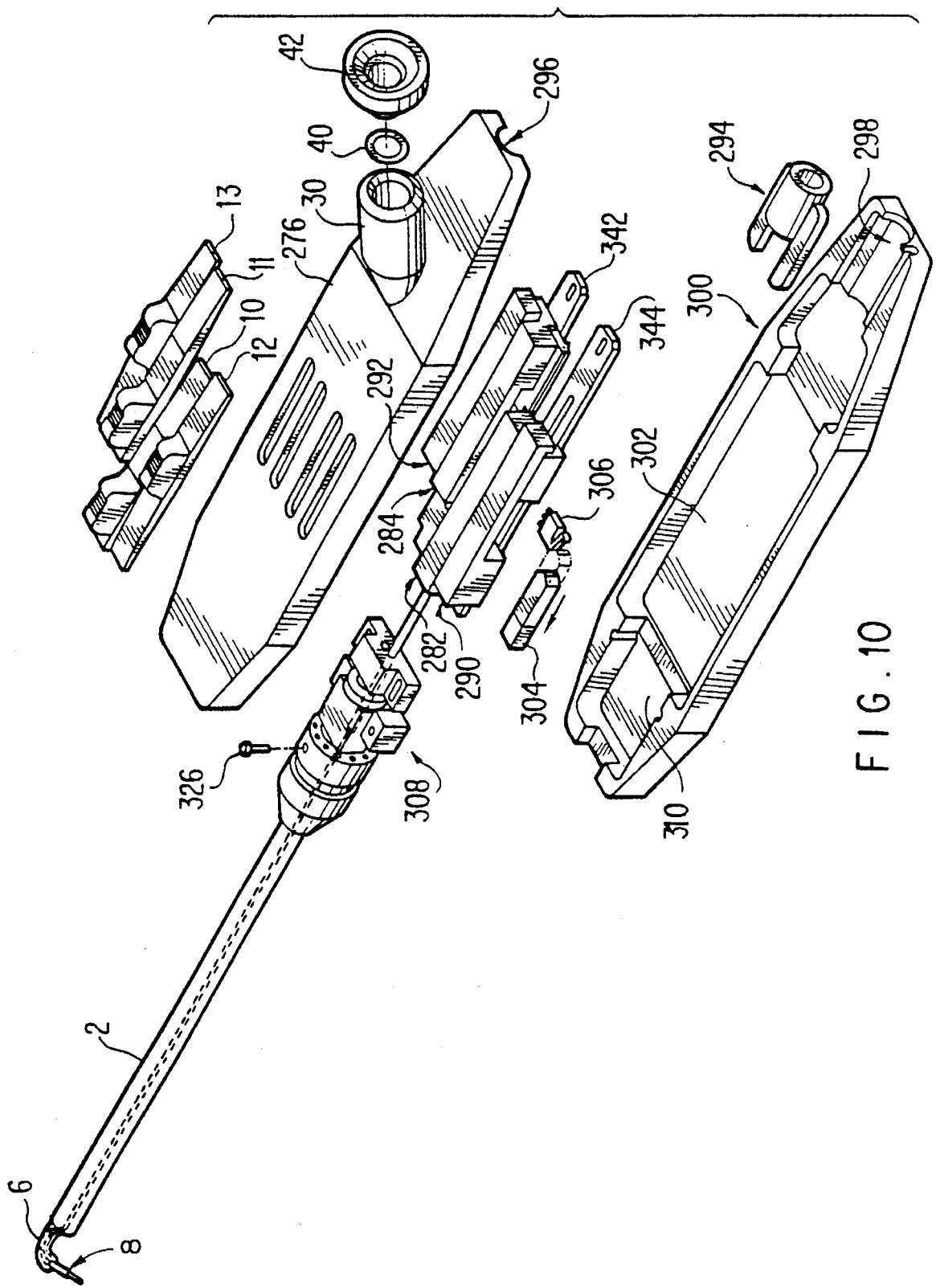
FIG. 10 is an exploded view of the RF ablation catheter shown in FIG. 1.

FIG. 10 is an exploded view of the RF ablation catheter assembly shown in FIG. 1. The upper handle plate 276 has two central slots 278 and 280 through which the electrode control slides 10 and 11 are attached to respective left electrode slide block 282 and right electrode slide block 284. Sleeve control slides 12 and 13 are attached through outer slots 286 and 288 to respective left sleeve slide block 290 and right sleeve slide block 292. Fiber optic receptor housing 30 is mounted on the proximal surface of the upper handle plate 276. The electrical receptor 294 is received in respective cavities 296 and 298 in the upper handle plate 276 and lower handle plate 300 attached thereto. The lower handle plate 300 has a central cavity 302 which accommodates the electrode and sleeve slide blocks and associated elements.

Microswitch activator blocks 304 (only left sleeve block shown) are connected to the sleeve slide blocks 290 and 292. They are positioned to actuate the microswitches 306 when the respective sleeve block (and sleeve attached thereto) have been advanced. The microswitches 306 hold the respective RF power circuits open until the respective sleeves are advanced to a position beyond the urethra wall and into the prostate to prevent direct exposure of the urethra to the energized RF electrodes. Extension of the sleeve 5 mm beyond the guide is usually sufficient to protect the urethra.

The tension-torque tube assembly 308 (see FIG. 11) is mounted in the distal end of the housing in the receptor 310.

FIG. 11 is an isometric view of the adjuster block and tension tube assembly 308 of the RF ablation catheter shown in FIG. 10. The torque tube 312 extends from the torque coupler 314 through the twist control knob 316 to the stylet guide 6. Bending flexure of the torque tube 312 during use lengthens the path from the handle to the guide tip 6. To prevent a resulting retraction of the stylet sleeve and electrode components when the torque tube 312 is flexed, a tension tube 318 having a fixed length and diameter smaller than the inner diameter of the torque tube 312 is provided.

The distal end of the tension tube 318 is securely attached to the stylet guide 6, and the proximal end 320 is secured to the adjuster block 322, for example, by an adhesive. The axial position of the adjuster block 322 can be adjusted to ensure the stylets 8 are initially positioned just inside the outlet ports in the stylet guide 6. Torque coupler 314 is mounted on the coupler block 324. Twist control knob stop pin 326 extends into a groove (not shown) and limits rotation of the control knob 316.

FIG. 12 is a detailed view "A" of the distal end tension tube connections of the tension tube shown in FIG. 11. The tension tube 318 is securely connected to the proximal end 328 of the stylet guide 6, for example by a length of shrink tubing 330.

Figure 13:
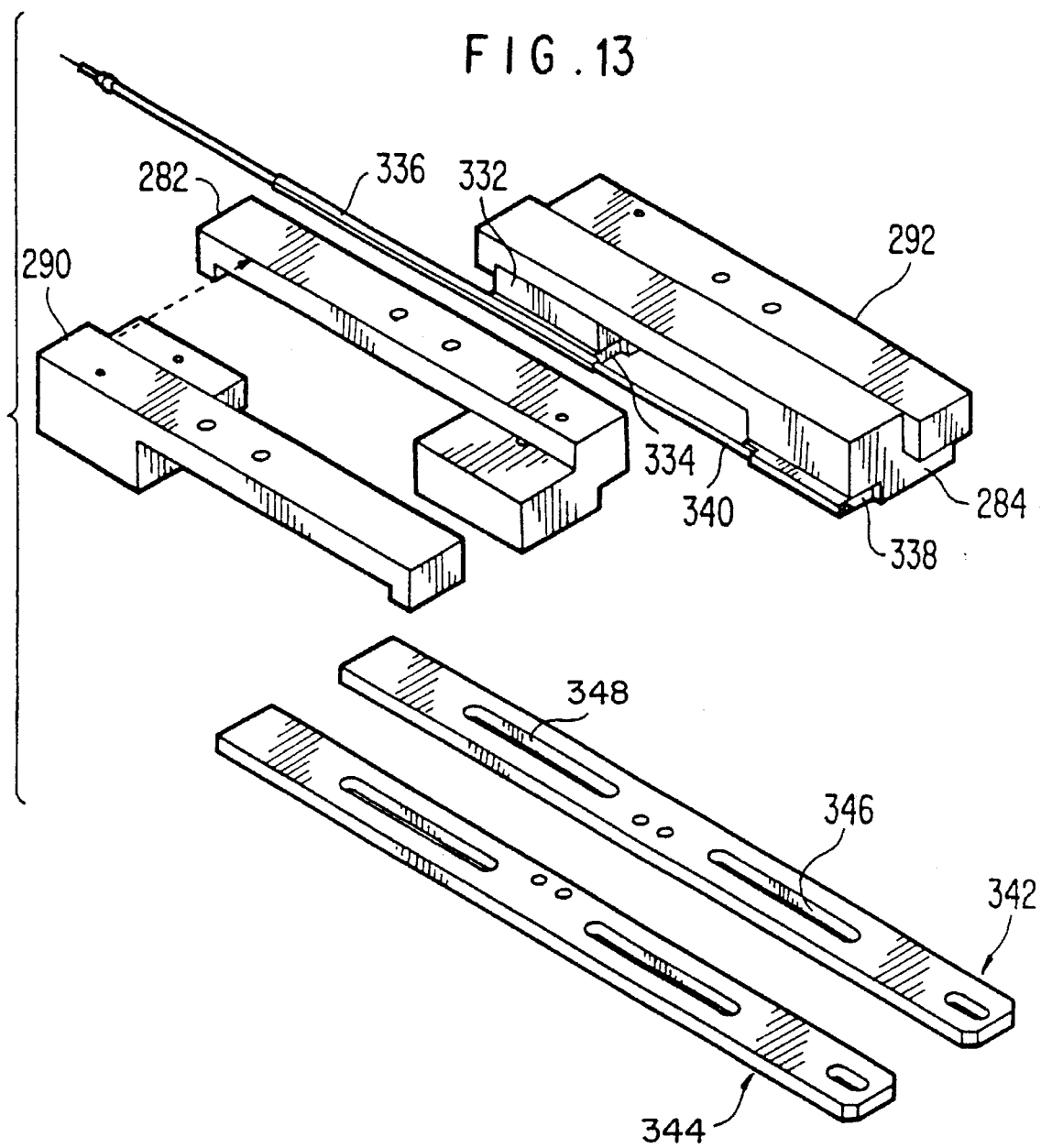
FIG. 13 is an exploded view of the sleeve and electrode slide block assembly of the embodiment shown in FIG. 10.

FIG. 13 is an exploded view of the sleeve and electrode slide block assembly of the embodiment shown in FIG. 10. The right sleeve slide block 292 has a projection 332 which extends inward under the right electrode slide block 284. Right sleeve connector 334 is mounted to the inner end of the projection 332, secured to the end of the proximal end of the sleeve 336. Right electrode connector 338 is attached to an inner surface of the electrode slide block 284 and is secured to the proximal end of electrode 340. The right sleeve and electrode slide blocks 292 and 284 are slidingly attached to the right friction adjustment rail 342 by screws (not shown) through slots 348 and 346, the screws being adjustable to provide sufficient friction between the blocks and the rail 342 to provide secure control over the stylet movement. The left sleeve slide block 290 and left electrode slide block 282 are mirror replicas of the right blocks and are similarly mounted on the left friction rail 344. The left sleeve and electrodes are not shown.

When the electrodes 8 in FIG. 1 are supplied with RF current via connector 16, the circuit from the electrodes to a grounding plate is closed. The current density flowing through the tissue passes through target tissues to be treated, creating lesions having the appropriate shape as seen in FIGS. 8 and 9. When two stylets are utilized, two overlapping lesions are created.

During the ablation procedure, the current density is greatest immediately adjacent the stylet electrodes and decreases in density as the distance increases from the stylets. It is possible during the ablation that the tissue immediately adjacent the stylet electrodes desiccates and possibly sticks to the stylet electrodes. Because the impedance of the tissue increases as the moisture content thereof decreases, this desiccation and sticking to the stylet necessitates an increase in applied power to maintain a predetermined level of ablation.

In order to avoid this happening, the operating surgeon can manipulate the slider blocks which operate the insulating sleeves surrounding the stylet electrodes. That is, the surgeon can move the slider handles 10 and 11 in FIG. 1 which, in turn, move the insulating sleeve (see FIG. 3) back and forth on stylet 32, for example. This longitudinal to and fro motion separates the tissue from the stylet and allows the natural body fluids and/or the flushing fluid to rehydrate the tissue and inhibit further desiccation of the surrounding tissue. This rehydration of the target tissue allows the ablation action to continue without interruption, which decreases the total time that the patient must undergo this procedure. Since the insulating sleeve 30 is soft and pliable, effective cleaning and scraping is not accomplished.

In order to decide when the operating surgeon should commence the to and fro action to unstick the stylets from surrounding tissue, the surgeon monitors the RF current flow from the stylet. When the current applied begins to drop during ablation, this is an indication that the tissue surrounding the stylet is drying out and possibly sticking directly to the stylet electrode. Engaging the slider handles in the distal and proximal directions in a forward and reverse action will unstick the tissue from the stylet, and allow moisture in the area to rehydrate the target tissue. This action will allow the ablation current to resume its former level and maintain the ablation action at the desired level.

Although preferred embodiments of the subject invention have been described in some detail, it is understood that obvious variations can be made without departing from the spirit and the scope of the invention as defined by the appended claims.

We claim:

1. A method for the treatment of benign prostatic hypertrophy of a prostate of a human male having a bladder with a base and a penis with a urethra therein formed by a urethral wall extending into the base of the bladder along a longitudinal axis with the prostate having tissue surrounding the urethra near the base of the bladder by the use of a radio frequency electrode formed of an electrically conductive material and being relatively rigid so that it can serve as a stylet and having a sharpened distal extremity serving as a tissue puncturing tip comprising the steps of introducing the radio frequency electrode into the urethra and advancing it longitudinally of the urethra along the longitudinal axis until the tip is in the vicinity of the prostate, thereafter advancing the radio frequency electrode in a direction at an angle to the longitudinal axis of the urethra to cause the radio frequency electrode to penetrate the urethral wall and to extend into the tissue of the prostate so that a preselected length of the radio frequency electrode including the tip is exposed to tissue in the prostate to thereby select a target volume of the tissue in the prostate surrounding the exposed length of the radio frequency electrode to be exposed to radio frequency energy, supplying radio frequency energy to the radio frequency electrode so that radio frequency energy is supplied to the selected target volume of the prostate surrounding the exposed length of the radio frequency electrode at a sufficient power level and for a sufficient period of time to raise the temperature of the tissue of the prostate in the selected target volume to cause ablation of the tissue in the selected target volume, separating ablated tissue from the radio frequency electrode while the radio frequency electrode is within the prostate, continuing the ablation of the tissue in the selected target volume and thereafter withdrawing the radio frequency electrode from the tissue of the prostate and out of the urethra whereby the separation of the ablated tissue from the radio frequency electrode improves the efficiency of the treatment.

2. A method as in claim 1 further comprising the step of ceasing the supply of radio frequency energy to the radio frequency electrode prior to the separating step and wherein the continuing step includes resuming the supply of radio frequency energy to the radio frequency electrode after the separating step.

3. A method as in claim 1 further comprising the step of monitoring the flow of radio frequency energy from the radio frequency electrode.

4. A method as in claim 3 wherein the separating step includes separating ablated tissue from the radio frequency electrode when the flow of radio frequency energy from the radio frequency electrode drops.

5. A method for the treatment of benign prostatic hypertrophy of a prostate of a human male having a bladder with a base and a penis with a urethra therein formed by a urethral wall extending into the base of the bladder along a longitudinal axis with the prostate having tissue surrounding the urethra near the base of the bladder by the use of a radio frequency electrode formed of an electrically conductive material and being relatively rigid so that it can serve as a stylet and having a sharpened distal extremity serving as a tissue puncturing tip and a sleeve slidably mounted on the radio frequency electrode movable to expose a preselected length of the radio frequency electrode comprising the steps of introducing the radio frequency electrode with the sleeve thereon into the urethra and advancing the radio frequency electrode longitudinally of the urethra until the tip is in the vicinity of the prostate, advancing the tip of the radio frequency electrode in a direction at an angle to the longitudinal axis of the urethra to cause the tip of the radio frequency electrode to penetrate the urethral wall and to extend into the target volume of the tissue of the prostate so that a preselected length of the radio frequency electrode extends beyond the urethral wall and is surrounded by a target volume of tissue and the sleeve extends through the urethral wall, supplying radio frequency energy to the radio frequency electrode at a sufficient power level and for a sufficient period of time to raise the temperature of the tissue of the prostate in the target volume to cause ablation of the tissue in the target volume, moving the sleeve distally along at least a portion of the preselected length of the radio frequency electrode to free ablated tissue from the radio frequency electrode and continuing the ablation of the tissue in the target volume.

6. A method as in claim 5 wherein the moving step includes moving the sleeve distally and then proximally along at least a portion of the preselected length of the radio frequency electrode.

7. A method for treatment of a prostate of a human male having a bladder with a base with a urethra formed by a urethral wall extending into the base of the bladder with the prostate having tissue surrounding the urethra near the base of the bladder by use of a medical probe device having an elongate member with proximal and distal extremities and a passageway extending from the proximal extremity to the distal extremity along a longitudinal axis, a flexible stylet assembly slidably mounted in the passageway in the elongate member and having a flexible distal extremity, the stylet assembly including a conductive electrode and a sleeve of insulating material surrounding the conductive electrode and permitting a predetermined portion of the conductive electrode to be exposed, and control means secured to the proximal extremity of the stylet assembly, the method comprising the steps of inserting the elongate member into the urethra until the distal extremity is in the proximity of the prostate, utilizing the control means to advance the distal extremity of the stylet assembly from a position within the passageway of the elongate member to a position outside of the passageway permitting the distal extremity of the stylet assembly to move outwardly in a direction which is at an angle with respect to the longitudinal axis so that the stylet assembly passes through the urethral wall and into the prostate with the conductive electrode being exposed in the tissue of the prostate, supplying radio frequency energy to the conductive electrode for causing ablation of the tissue in the prostate, moving the insulating sleeve distally and then proximally along at least a portion of the conductive electrode being exposed in the tissue of the prostate to rehydrate ablated tissue in the vicinity of the conductive electrode, continuing the ablation of the tissue in the prostate and thereafter withdrawing the stylet assembly from the prostate and the urethral wall into the passageway and removing the elongate member from the urethra.

8. A method as in claim 7 further comprising the step of causing relative movement between the insulating sleeve and the conductive electrode to expose a desired length of the conductive electrode while having the insulating sleeve extend a sufficient distance beyond the urethral wall so that the urethral wall is protected by the insulating sleeve from radio frequency energy during the supply of radio frequency energy to the conductive electrode.

9. A method as in claim 7 further comprising the step of ceasing the supply of radio frequency energy to the conductive electrode prior to the moving step and wherein the continuing step includes resuming the supply of radio frequency energy to the conductive electrode after the moving step.

10. A method as in claim 7 further comprising the step of monitoring the flow of radio frequency energy from the conductive electrode.

11. A method as in claim 10 wherein the moving step includes rehydrating ablated tissue in the vicinity of the conductive electrode when the flow of radio frequency energy from the conductive electrode drops.

12. A medical probe device for medical treatment of tissue at a treatment site through a natural body opening defined by a wall comprising a guide housing having proximal and distal extremities and having a passageway extending from the proximal extremity to the distal extremity, a stylet slidably mounted in the passageway and including a flexible conductive electrode with a sharpened tip and an insulating sleeve slidably mounted on the electrode but exposing the sharpened tip, means carried by the distal extremity of the guide housing and in communication with the passageway for directing the electrode and the insulating sleeve sidewise of the guide housing, handle means mounted on the proximal extremity of the guide housing for introducing the distal extremity of the guide housing into the natural body opening to a position adjacent the treatment site, means mounted on the proximal extremity of the guide housing for advancing the stylet to cause the sharpened tip of the electrode to penetrate the wall and extend into the tissue at the treatment site with the insulating sleeve extending through the wall and means for supplying electrical energy to the electrode to cause a thermal effect in the tissue at the treatment site, the means for advancing the stylet including means for moving the insulating sleeve distally and then proximally along at least a portion of the electrode to free the electrode from ablated tissue which has adhered to the electrode.

13. A medical probe device as in claim 12 further comprising means for measuring the flow of electrical energy from the electrode.

14. A medical probe device as in claim 12 for the treatment by radio frequency ablation of a target volume in prostatic tissue of a prostate of a human male having a bladder with a base and a penis with a urethra therein formed by a urethral wall extending into the base of the bladder along a longitudinal axis with the tissue of the prostate surrounding the urethra near the base of the bladder further comprising an additional stylet slidably mounted in the passageway and of the same type as the first named stylet whereby the handle means introduces the distal extremity of the guide housing into the urethra to a position adjacent the prostate and the means mounted on the proximal extremity of the guide housing advances the stylets to cause the sharpened tip of the electrodes to penetrate the urethral wall and to extend into a selected target volume of the prostate with the insulating sleeves extending through the urethral wall and whereby the means for supplying electrical energy to the electrodes causes a thermal effect in the selected target volume of the prostate, the means for advancing the stylets including means for moving the insulating sleeves distally and then proximally along at least a portion of the electrodes to free the electrodes from ablated tissue which has adhered to the electrodes.

* * * * *